(12) United States Patent
Bara et al.

(10) Patent No.: US 6,677,857 B2
(45) Date of Patent: Jan. 13, 2004

(54) REFRIGERATED CABINET FOR STORING BIOLOGICAL ARTICLES EQUIPPED WITH MEANS FOR CONTROLLING THE CABINET CONTENTS

(76) Inventors: Nicolas Bara, 4 place du Puits, F-60240 Villetertre (FR); Jean-Claude Diot, 9 résidence Le Parc, F-51500 Ludes (FR); Dominique Lambert, 34 bis rue des Voltigeurs, F-95520 Osny (FR)

( * ) Notice: Subject to any disclaimer, the term of this patent is extended or adjusted under 35 U.S.C. 154(b) by 0 days.

(21) Appl. No.: 09/865,631

(22) Filed: May 25, 2001

(65) Prior Publication Data

US 2002/0023441 A1 Feb. 28, 2002

Related U.S. Application Data

(63) Continuation of application No. PCT/FR99/03015, filed on Dec. 3, 1999.

(30) Foreign Application Priority Data

Dec. 3, 1998 (FR) ............................................. 98 15297

(51) Int. Cl.[7] ................................................ G08B 13/14
(52) U.S. Cl. ................. 340/572.1; 340/5.92; 340/545.6
(58) Field of Search ........................... 340/572.1, 568.1, 340/545.6, 5.92, 10.1; 235/385; 705/22, 28; 62/125

(56) References Cited

U.S. PATENT DOCUMENTS

| 5,287,414 A | * | 2/1994 | Foster .................... 235/385 X |
| 5,721,531 A | * | 2/1998 | Garver et al. ......... 340/572.1 X |
| 5,751,221 A | * | 5/1998 | Stanfield et al. ...... 340/572.1 X |
| 5,936,527 A | * | 8/1999 | Isaacman et al. ......... 340/572.1 |
| 5,969,606 A | * | 10/1999 | Reber et al. ................. 340/540 |
| 5,977,875 A | * | 11/1999 | Lin et al. .............. 340/572.1 X |
| 6,204,763 B1 | * | 3/2001 | Sone ........................ 340/568.1 |
| 6,204,764 B1 | * | 3/2001 | Maloney .............. 340/572.1 X |
| 6,285,282 B1 | * | 9/2001 | Dorenbosch et al. 340/572.1 X |
| 6,294,997 B1 | * | 9/2001 | Paratore et al. .......... 340/572.1 |
| 6,327,576 B1 | * | 12/2001 | Ogasawara .................. 705/22 |
| 6,332,098 B2 | * | 12/2001 | Ross et al. .................. 700/226 |
| 2002/0026325 A1 | * | 2/2002 | Hirahara et al. ...... 340/572.1 X |

FOREIGN PATENT DOCUMENTS

| DE | 298 12 877 U 1 | 10/1998 |
| EP | 0 142 688 | 5/1985 |
| EP | 0 851 377 A1 | 7/1998 |
| JP | 10009753 | 1/1968 |
| JP | 10316210 | 12/1998 |

* cited by examiner

Primary Examiner—Thomas Mullen
(74) Attorney, Agent, or Firm—Piper Rudnick LLP

(57) ABSTRACT

A thermostated cabinet for storing articles fitted with radio-frequency identifier including a cabinet having an opening for introducing and removing articles, an article monitor comprising at least one radio-frequency receiver connected to at least one antenna for detecting movements of the articles, and means for providing data to the radio frequency identifier.

19 Claims, 1 Drawing Sheet

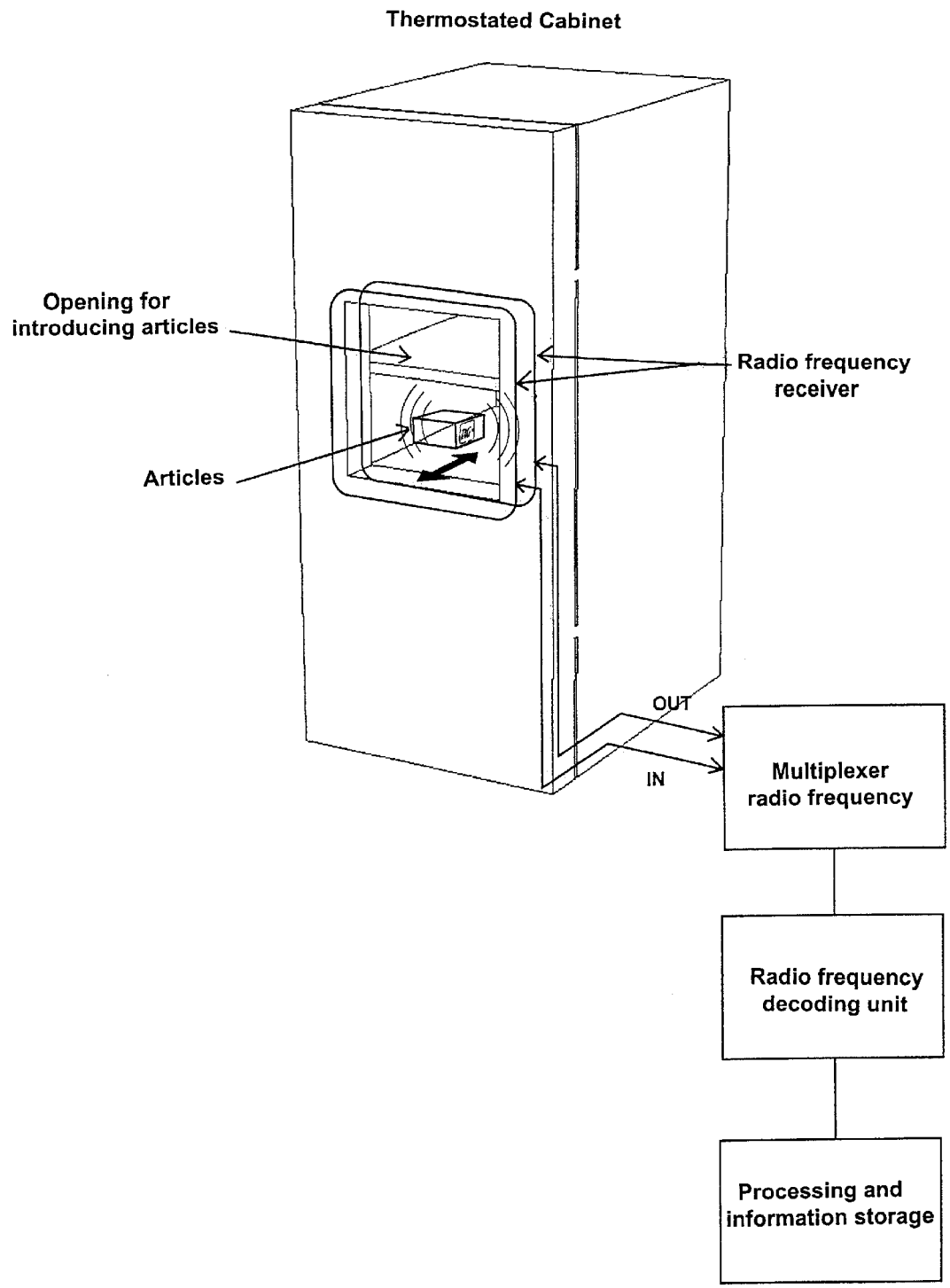

REFRIGERATED CABINET FOR STORING BIOLOGICAL ARTICLES EQUIPPED WITH MEANS FOR CONTROLLING THE CABINET CONTENTS

RELATED APPLICATION

This is a continuation of International Application No. PCT/FR99/03015, with an international filing date of Dec. 3, 1999, which is based on French Patent Application No. 98/15297, filed Dec. 3, 1998.

FIELD OF THE INVENTION

This invention pertains to the field of the storage and preservation of products in a thermostated cabinet, especially in a refrigerator or freezer. It pertains more specifically to the field of storing biomedical reagents and consumables, the preservation of organs for transplantation, which exhibit low tolerance to thermal variations and require rigorous management of the stored products.

BACKGROUND

Known in the state of the art is DE 29812877 which describes a refrigerator comprising a means for reading a transponder element affixed to the refrigerated products, in which the transponder element has an identification code. Also known is JP 10316210 which describes a refrigerator for storing food products, as well as EP 142688 and EP 851377.

These types of equipment can not be employed for the management of biological products which require a high degree of rigor with respect to the conditions of use and the thermal cycles. For this type of biological product, robotized thermostated cabinets have been proposed in the state of the art. These cabinets have electromechanical manipulators, controlled by a computer which stores in memory the movements of the products that are handled. This type of equipment is very expensive and is not completely reliable. In fact, a voluntary or involuntary change in the placement of the products in the cabinet severely disturbs the processing of the information which is solely based on the position of the manipulator arm at the moment when each product is deposited. If the position is changed other than by the manipulator arm, the calculator is unaware of this change and provides erroneous information.

It would accordingly be advantageous to resolve these disadvantages by providing a more reliable device, the additional cost of which—compared to a simple thermostated cabinet or cell—is small, and which enables rigorous management of the conditions of use and perfect traceability of the operating conditions. It would especially be advantageous to enable an irreversible association between the data relative to the life of the product and the product in question, and guarantee a continuity of information to enable reliable exploitation by other devices.

SUMMARY OF THE INVENTION

This invention relates to a thermostated cabinet for storing articles fitted with a radio-frequency identifier including a cabinet having an opening for introducing and removing articles, an article monitor comprising at least one radio-frequency receiver connected to at least one antenna for detecting movements of the articles, and means for providing data to the radio-frequency identifier.

BRIEF DESCRIPTION OF THE DRAWING

The drawing is a schematic perspective view of a thermostated cabinet for storing articles in accordance with aspects of the invention.

DETAILED DESCRIPTION

As shown by way of example in the Drawing, the invention pertains in its broadest sense to a refrigerated cabinet for the storage of products, which cabinet is fitted with an opening for the introduction and removal of products, and means for monitoring the contents of the cabinet, characterized in that the monitoring means is constituted of at least one radio-frequency receiver connected to an antenna. This antenna is advantageously located in the vicinity of the cabinet opening to enable detection of the movements of the products fitted with a radio-frequency identification means. The cabinet in accordance with the invention can be in the form of a transportable chest or cell.

The invention furthermore advantageously comprises a means for activating the RF identification means of the products. The means for activating the RF identification means of the products is preferably controlled by an opening detector for the cabinet's door.

According to an advantageous variant, the invention further comprises a computer for recording information relative to the identity of the products whose presence is detected in correlation with the temporal information provided by a clock. According to another variant, the invention further comprises signaling means activated by the removal of a product for a duration of time greater than a predetermined value. According to still another variant, the invention further comprises signaling means activated by a product counter controlled by the detection of the RF identification means associated with each product.

According to one variant, the product comprises a memory designed to record information relative to the storage conditions, especially dated information, to ensure traceability of the products.

The invention also pertains to temperature-sensitive products to be stored in a refrigerated cabinet, with each product bearing a specific RF identification label. This label furthermore preferably comprises a memory in which are recorded data relative to the storage and/or transport conditions.

Each product advantageously also comprises a temperature sensor controlling the identifier status transmitted by the RF label. According to one specific variant, the RF label comprises an antenna and an integrated circuit with an RF stage, an RF signal modulation stage and a memory containing a specific identification sequence for personalization of the modulation signal. According to another specific variant, the product according to the invention is formed by a container equipped with an RF identification label.

Better understanding of the invention will be obtained by reading the description below with reference to a nonlimitative example of implementation.

The cabinet is constituted by a frigorific cabinet closed by a door. The cabinet has trays for receiving different products, for example, organs intended for transplantation, blood bags, biochemical reagents and biological products. These products are especially blood bags bearing read-write RF labels or laboratory consumables with an RF integrated or hybrid circuit or a serotheque with an RF circuit. Each tray has a detection antenna such that it can query the radio-frequency labels carried by the stored products.

The detection antenna transmits entry and departure information for each labeled consumable or product to a computer equipped with a memory and a clock. This information makes it possible to know at all times:

the position of the different products in the refrigerator,
the departure time of the product, the storage status, the preservation conditions.

Reading the radio-frequency labels can be activated on a periodic basis or, preferably, by the contactor relay detecting the opening of the door. This equipment makes it possible to substantially guarantee the traceability of the refrigerated products, including when they are transported in other equipment fitted with means for reading the RF label of the product.

The radio-frequency labels with which the products are fitted can be labels comprising a microcomputer in the form of an integrated circuit powered by a battery or an H.F. loop, as well as an antenna. There is possibly a memory intended to record the information transmitted by the introduced products which makes it possible to exchange status information from a product originating from a different cabinet. They can also comprise a temperature or hygrometry sensor.

The microcomputers furthermore comprise a memory zone for the registration of personalization information enabling control of the signal sequence transmitted at the moment of label activation. When the RF labels fitted to the products intended to be refrigerated are equipped with a memory, the memory enables registration of information relative to the thermal cycles, in the form of a file comprising an identifier, for example, the date and time of the beginning of a period, the thermal conditions and, possibly, alarm data. The address of a new cycle can be triggered by the refrigerated equipment or on a periodic basis, or by opening the door.

The RF label can be an emission and reception label, or a simple emission label, or a simple reception label.

In the first case or the third case, the memory of the label records the data provided by the equipment in response to the activation produced upon introduction of the product in the refrigerated cabinet.

In the second case, the memory records the data upon activation of the emission signal.

What is claimed is:

1. A system for storing and monitoring articles fitted with a radio-frequency identifier comprising:
    a thermostated cabinet having an opening for introducing and removing said articles;
    an article monitor comprising at least one radio-frequency receiver connected to at least one antenna for detecting movements of said articles;
    means for providing data to said radio-frequency identifier; and
    a computer for recording information relative to 1) identity of said articles, the presence of which is detected in correlation with temporal information provided by a clock, 2) position of said articles in said cabinet, 3) storage status of said articles, and 4) preservation conditions of said articles.

2. The system according to claim 1, further comprising means for activating said radio frequency identifier.

3. The system according to claim 1, further comprising signalization means activated by removal of at least one of said articles for a duration of time greater than a predetermined value.

4. The system of claim 1, wherein said radio-frequency identifier comprises an RF identification label and a memory for recording storage data.

5. The system according to claim 4, further comprising a temperature sensor controlling identifier status signal transmitted by said RF identification label.

6. The article according to claim 4, wherein said memory records information relative to storage conditions.

7. The according to claim 1, wherein said radio-frequency identifier comprises a container equipped with an RF identification label.

8. The system according to claim 1, wherein said thermostated cabinet is refrigerated.

9. A system for storing and monitoring articles fitted with a radio-frequency identifier comprising:
    a thermostated cabinet having an opening for introducing and removing said articles;
    an article monitor comprising at least one radio-frequency receiver connected to at least one antenna for detecting movements of said articles;
    means for activating said radio-frequency identifier; and
    means for providing data to said radio-frequency identifier, wherein the means for activating said radio frequency identifier is controlled by a cabinet door opening detector.

10. A system for storing and monitoring articles fitted with a radio-frequency identifier comprising:
    a thermostated cabinet having an opening for introducing and removing said articles;
    an article monitor comprising at least one radio-frequency receiver connected to at least one antenna for detecting movements of said articles; and
    means for providing data to said radio-frequency identifier, further comprising a computer for recording information relative to identity of said articles, the presence of which is detected in correlation with temporal information provided by a clock and signalization means activated by removal of at least one of said articles for a duration of time greater than a predetermined value, wherein said signalization means is activated by an article counter controlled by detection of said radio frequency identifier associated with said article.

11. A system for storing and monitoring articles fitted with a radio-frequency identifier comprising:
    a thermostated cabinet having an opening for introducing and removing said articles;
    an article monitor comprising at least one radio-frequency receiver connected to at least one antenna for detecting movements of said articles; and
    means for providing data to said radio-frequency identifier, wherein said radio-frequency identifier label comprises an antenna and an integrated circuit comprising an RF stage, an RF signal modulation stage and a memory having a specific identification sequence for personalization of the modulation signal.

12. A system for preserving biological products comprising:
    a multiplicity of said biological products fitted with RF identification labels;
    a thermostated cabinet having an opening for introducing and removing said biological products;
    means for monitoring contents of said thermostated cabinet comprising at least one radio-frequency receiver connected to at least one antenna for detection of movements of said biological products which are fitted with a radio-frequency identification means;
    means to supply data to said radio-frequency identification means; and
    a memory for recording storage data.

13. The system according to claim 12, wherein said thermostated cabinet is refrigerated.

14. A system for storing and monitoring articles fitted with a radio-frequency identifier comprising:

a thermostated cabinet having an opening for introducing said articles;

an article monitor comprising at least one radio-frequency receiver connected to at least one antenna;

a cabinet opening detector connected to said article monitor for activating said radio-frequency identifier; and means for providing data to said radio-frequency identifier.

15. A system for storing and monitoring articles fitted with a radio-frequency identifier comprising:

a thermostated cabinet in the form of a transportable chest or cell having an opening for introducing and removing said articles;

an article monitor comprising at least one radio-frequency receiver connected to at least one antenna for detecting movements of said articles;

a computer for recording information relative to the identity of said articles, the presence of which is detected by said article monitor in connection with temporal information provided by a clock;

a signalization means activated by removal of at least one of said articles for a duration of time greater than a predetermined value; and means for providing data to said radio-frequency identifier, wherein said signalization means is activated by an article counter controlled by detection of said radio-frequency identifier associated with said article.

16. A system for storing articles comprising:

a thermostated cabinet having an opening for introducing and removing said articles;

an article monitor having at least one radio-frequency receiver connected to at least one antenna for detecting movement of said articles;

a radio frequency identifier attachable to said articles, said radio-frequency identifier comprising an RF identification label and a memory for recording storage data;

means for providing data to said radio-frequency identifier; and a computer for recording information relative to 1) identity of said articles, the presence of which is detected in correlation with temporal information provided by a clock, 2) position of said articles in said cabinet, 3) storage status of said articles, and 4) preservation conditions of said articles.

17. The system according to claim 16, further comprising a temperature sensor controlling identifier status signal transmitted by said RF identification label.

18. A system for storing and monitoring articles comprising:

a thermostated cabinet having an opening for introducing and removing said articles;

an article monitor comprising at least one radio-frequency receiver connected to at least one antenna for detecting movement of said articles;

a radio-frequency identifier attachable to said articles, said radio-frequency identifier comprising an antenna and an integrated circuit having an RF stage, RF signal modulation stage and a memory having a specific identification sequence for personalization of the modulation signal; and means for providing data to said radio-frequency identifier.

19. A system for storing and monitoring articles comprising:

a thermostated cabinet having an opening for introducing and removing said articles;

an article monitor comprising at least one radio-frequency receiver connected to at least one antenna for detecting movement of said articles;

a radio-frequency identifier attachable to said article, said radio-frequency identifier comprising a container equipped with an RF identification label; and a computer for recording information relative to 1) identity of said articles, the presence of which is detected in correlation with temporal information provided by a clock, 2) position of said articles in said cabinet, 3) storage status of said articles, and 4) preservation conditions of said articles.

* * * * *